(12) United States Patent
Lee et al.

(10) Patent No.: US 12,293,899 B2
(45) Date of Patent: May 6, 2025

(54) PLASMA GENERATION DEVICE COMPRISING POROUS CERAMIC DIELECTRIC

(71) Applicant: KOREA INSTITUTE OF MATERIALS SCIENCE, Changwon-si (KR)

(72) Inventors: Seung-hoon Lee, Changwon-si (KR); Do-geun Kim, Seoul (KR); Chang-su Kim, Changwon-si (KR); Hun-kwan Park, Changwon-si (KR)

(73) Assignee: KOREA INSTITUTE OF MATERIALS SCIENCE, Changwon-si (KR)

( * ) Notice: Subject to any disclaimer, the term of this patent is extended or adjusted under 35 U.S.C. 154(b) by 572 days.

(21) Appl. No.: 17/776,291

(22) PCT Filed: Oct. 14, 2020

(86) PCT No.: PCT/KR2020/014016
§ 371 (c)(1),
(2) Date: May 12, 2022

(87) PCT Pub. No.: WO2021/096077
PCT Pub. Date: May 20, 2021

(65) Prior Publication Data
US 2022/0406570 A1    Dec. 22, 2022

(30) Foreign Application Priority Data

Nov. 14, 2019    (KR) .................. 10-2019-0145658

(51) Int. Cl.
*H05H 1/24* (2006.01)
*H01J 37/32* (2006.01)

(52) U.S. Cl.
CPC .. *H01J 37/32348* (2013.01); *H01J 37/32871* (2013.01); *H05H 1/2425* (2021.05); *H05H 1/2441* (2021.05)

(58) Field of Classification Search
None
See application file for complete search history.

(56) References Cited

U.S. PATENT DOCUMENTS

| | | | |
|---|---|---|---|
| 2003/0007904 A1* | 1/2003 | Tonkovich | B01J 37/0244 422/177 |
| 2003/0050196 A1* | 3/2003 | Hirano | B01J 21/06 507/238 |
| 2004/0265166 A1* | 12/2004 | Petcu | A61L 2/14 422/23 |

(Continued)

FOREIGN PATENT DOCUMENTS

| | | |
|---|---|---|
| JP | 06-015143 | 1/1994 |
| JP | 2000-271198 | 10/2000 |

(Continued)

*Primary Examiner* — Jason Berman
(74) *Attorney, Agent, or Firm* — LEX IP MEISTER, PLLC

(57) ABSTRACT

This disclosure relates to a plasma generator including a porous ceramic dielectric. More specifically, this disclosure relates to a plasma generator for air purification capable of effectively generating ozone for removing bacteria, viruses, etc., and minimizing pressure loss while increasing air purification capacity by including a porous ceramic dielectric coated with an antibacterial material.

16 Claims, 4 Drawing Sheets

(56) References Cited

U.S. PATENT DOCUMENTS

2005/0214181 A1* 9/2005 Kaneko .................. B01D 53/32
422/186.04

FOREIGN PATENT DOCUMENTS

| JP | 2009-208025 | | 9/2009 |
|----|----|----|----|
| JP | 2010-069346 | | 4/2010 |
| JP | 2010069346 A | * | 4/2010 |
| JP | 2013-154145 | | 8/2013 |
| KR | 10-0483417 | | 4/2005 |
| KR | 10-0956844 | | 5/2010 |
| KR | 101818947 | | 1/2018 |

* cited by examiner

PLASMA GENERATION DEVICE COMPRISING POROUS CERAMIC DIELECTRIC

TECHNICAL FIELD

This disclosure relates to a plasma generator comprising a porous ceramic dielectric. More specifically, this disclosure relates to a plasma generator for air purification capable of effectively generating ozone for removing bacteria, viruses, etc., and minimizing pressure loss while increasing air purification capacity by comprising a porous ceramic dielectric coated with an antibacterial material.

BACKGROUND ART

As the ventilation cycle decreases due to an increase in outdoor fine dust and ultrafine dust concentration, indoor air pollution caused by bio-aerosols generated by humans and animals, volatile organic compounds and radon emitted from building materials, and fine dust generated during food cooking is getting worse.

In particular, the problem of indoor air pollution due to bio-aerosols or pathogens, which comprehensively means microorganisms such as bacteria and fungi, viruses, etc., is serious. For example, as seen in the case of middle east respiratory syndrome (MERS), there is a problem in that the occurrence of secondary infections may rapidly increase due to the lack of management skills for pathogens in the indoor air of public facilities.

As the social demand for a safe and healthy living environment increases, the need for a new concept material for air purification capable of effectively collecting and sterilizing bio-aerosols is increasing.

Polymer fiber-based filter materials currently used for air purification are capable of collecting bacteria, adsorbing VOCs, and collecting fine dust in the size of several hundred nanometers to several tens of micrometers, but it is difficult to prevent odors due to bacterial growth in the filter and secondary infection due to airborne microorganisms.

In addition, the UV sterilization method, known as bio-aerosol management technology, has a problem of lowering the pathogen removal performance and shortening the lifespan due to curing of the polymer filter when the UV sterilization method is mixed with a polymer fiber-based filter.

Therefore, in order to prevent damage such as secondary infection caused by bio-aerosol in public facilities such as hospitals, there is a need to develop the development of materials capable of optimizing indoor air quality according to the characteristics of the space in public facilities, and collecting and sterilizing the bio-aerosols.

As a background art of this disclosure, Korean Patent Registration No. 1818947 discloses an air purification ion generator for removing fine dust.

DISCLOSURE

Technical Problem

An object of this disclosure is to provide a plasma generator with excellent bio-aerosol collection and sterilization performance.

Another object of this disclosure is to provide a plasma generator capable of maximizing air purification capacity while minimizing pressure loss in a large air purifier.

Another object of this disclosure is to provide a plasma generator capable of optimizing indoor air quality according to characteristics of spaces in public facilities.

Another object of this disclosure is to provide a plasma generator including a ceramic filter coated with an antibacterial material capable of implementing antibacterial properties even under conditions in which plasma and ozone are not generated.

Another object of this disclosure is to provide a plasma generator capable of minimizing ozone emission.

Another object of this disclosure is to provide a plasma generator capable of increasing an area in order to be applicable to commercial air conditioning facilities.

Other objects and advantages of this disclosure will become more apparent from the following detailed description, claims, and drawings of this disclosure.

Technical Solution

In one general aspect, a plasma generator includes: a plasma generating module including a first ground electrode, a high voltage electrode, and a first ceramic layer made of a porous ceramic dielectric formed between the first ground electrode and the high voltage electrode, in which the first ground electrode and the high voltage electrode are made of a grid-like or porous metal, and the ceramic includes an antibacterial coating layer coated with an antibacterial material, and the first ceramic layer is provided with an open pore.

The plasma generating module may further include a second ceramic layer made of a porous ceramic dielectric provided on one side of the high voltage electrode, and a second ground electrode provided on one side of the second ceramic layer.

The plasma generating module may further include a second ground electrode provided on one side of the high voltage electrode.

A porosity of the first ground electrode and the high voltage electrode may be 5 to 95 vol %.

A thickness of the first ground electrode or the high voltage electrode may be 0.1 to 10 mm.

The first ceramic layer may be formed as a single layer.

The ceramic may include at least one of alumina ($Al_2O_3$), zirconia ($ZrO_2$), diatomaceous earth, and silica ($SiO_2$).

An antibacterial coating layer of the ceramic may include at least one of zinc oxide having antibacterial activity and a carbon compound converting ozone into hydroxide.

The zinc oxide may include $ZnO_x$, wherein x is 1 to 2.

The carbon compound may convert ozone into OH active species.

The ceramic may be a bead or reticulated porous ceramic.

A pore density of the reticulated porous ceramic may be 30 to 100 pores per inch (PPI).

The plasma generator may include: a first ceramic layer made of a bead and a second ceramic layer made of the bead, a first ceramic layer made of a bead and a second ceramic layer made of a reticulated porous ceramic, a first ceramic layer made of a reticulated porous ceramic and a second ceramic layer made of a bead, or a first ceramic layer made of a reticulated porous ceramic and a second ceramic layer made of the reticulated porous ceramic.

A particle size of the bead may be 100 to 5000 μm.

A porosity of at least one of the first ceramic layer made of the bead and the second ceramic layer made of the bead may be 0.5 to 50 vol %.

A porosity of at least one of the first ceramic layer made of the reticulated porous ceramic and the second ceramic layer made of the bead may be 0.5 to 50 vol %.

In another general aspect, there is provided an air purifier including the plasma generator of this disclosure.

The air purifier may further include an ozone removal catalyst unit behind the plasma generator.

A wind speed of the air purifier may be 0.1 to 5 m/s.

Advantageous Effects

According to one embodiment, it is possible to effectively generate ozone to remove bacteria, viruses, etc., and minimize pressure loss while increasing air purification capacity by including a porous ceramic dielectric coated with an antibacterial material.

According to an embodiment, it is possible to optimize indoor air quality according to spatial characteristics of a large public facility by adjusting a size of bead and an arrangement, a thickness, or the like of electrodes according to characteristics of the space.

According to an embodiment, it is possible to increase an area of a plasma generator by simplifying the structure and manufacturing process of the plasma generator.

According to an embodiment, it is possible to minimize harmful ozone emission by applying various antibacterial members capable of decomposing ozone to a coating layer of a porous ceramic dielectric.

According to an embodiment, it is possible to provide a plasma generator including a ceramic filter coated with an antibacterial material capable of implementing antibacterial properties even under conditions in which plasma and ozone are not generated.

According to an embodiment, it is possible to provide a plasma generator capable of easily being applied to commercial air conditioning facilities.

According to an embodiment, it is possible to provide a plasma generator capable of efficiently removing specific pathogens by applying various sterilizing materials to a coating layer of a porous ceramic dielectric.

BEST MODE

Figure 1A:
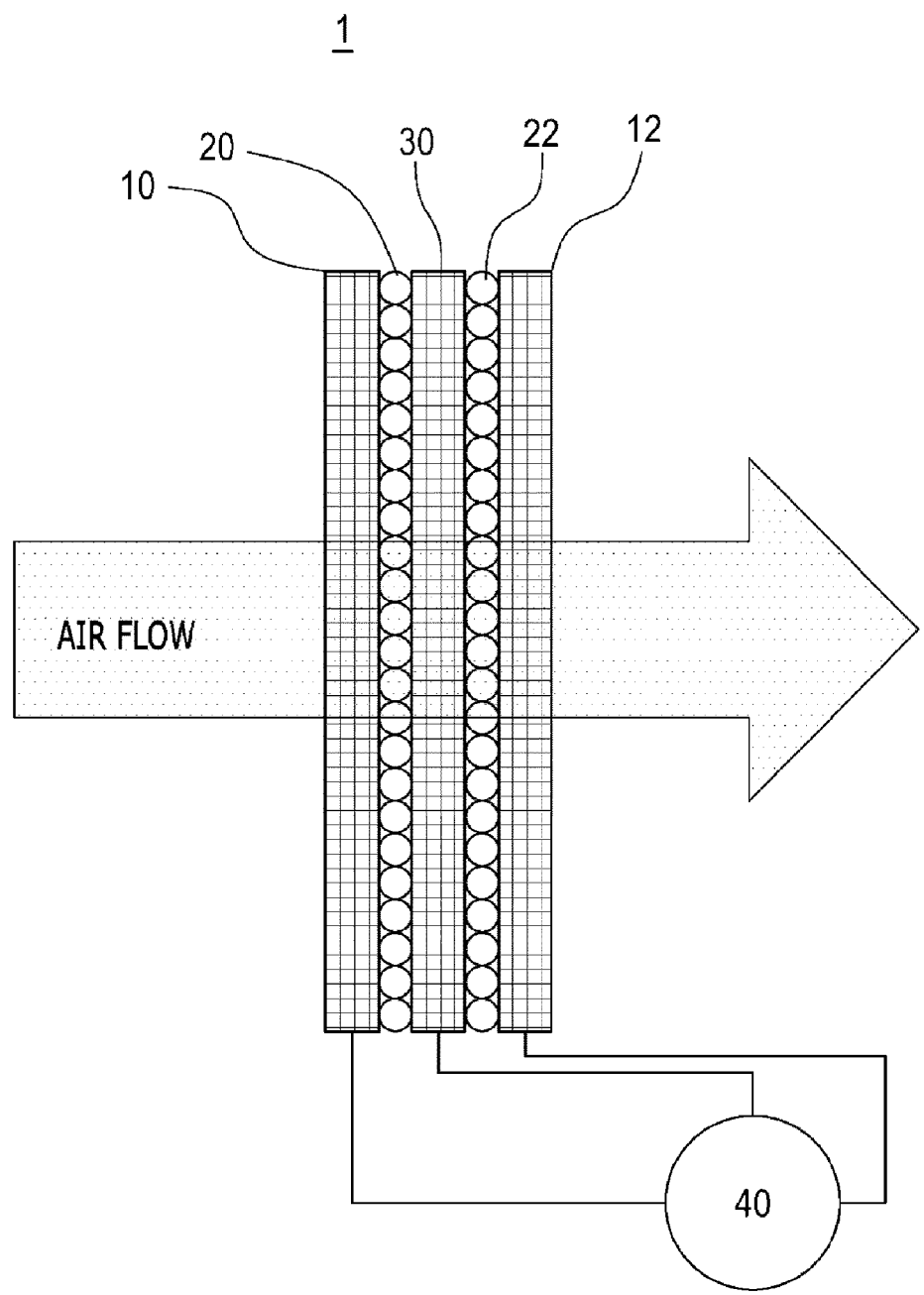
FIG. 1A is a diagram schematically illustrating a plasma generator according to an embodiment of this disclosure.

The above object and means of this disclosure and the effects thereof will become more obvious from the following detailed description associated with the accompanying drawings. Therefore, those skilled in the art to which this disclosure pertains may easily practice a technical idea of this disclosure. In addition, in describing this disclosure, when a detailed description of well-known technology relating to this disclosure may unnecessarily make unclear the spirit of this disclosure, a detailed description thereof will be omitted.

Terms used in the present specification are for explaining embodiments rather than limiting this disclosure. Unless otherwise stated, a singular form includes a plural form in the present specification. In this specification, terms such as "include," "comprise,", "provide," or "have" do not exclude presence or addition of one or more other elements other than the mentioned elements.

In this specification, terms such as "or," and "at least one," may indicate one of the words listed together, or a combination of two or more. For example, "A or B" or "at least one of A and B" may include only one of A or B, or both A and B.

In this specification, descriptions according to "for example" and the like may not exactly match the presented information, such as recited properties, variables, or values, and should not be construed as limiting the embodiments of this disclosure according to various embodiments of this disclosure with effects such as variations, including tolerances, measurement errors, limits of measurement accuracy, and other factors commonly known.

In the present specification, it is to be understood that when one component is referred to as being "connected to" or "coupled to" another component, one component may be connected directly to or coupled directly to another component or be connected to or coupled to another component with the other component interposed therebetween. On the other hand, it is to be understood that when one element is referred to as being "connected directly to" or "coupled directly to" another element, it may be connected to or coupled to another element without the other element intervening therebetween.

In this specification, when a component is described as being "on" or "contacting" another component, it may be directly in contact with or connected to other components, but it should be understood that another component may exist therebetween. On the other hand, when any component is described as being "directly on" or "directly contact with" other components, it may be understood that another element does not exist therebetween. Other expressions describing the relationship between the components, for example, "~between", "~directly between", and the like can be interpreted similarly.

In the present specification, terms 'first', 'second', and the like, may be used to describe various components, but the components are not to be construed as being limited by these terms. In addition, the above term should not be construed as limiting the order of each component, and may be used for the purpose of distinguishing one component from another. For example, a "first component" may be named a "second component" and the "second component" may also be similarly named the "first component."

Unless defined otherwise, all terms used in the present specification have the same meaning as meanings commonly understood by those skilled in the art to which this disclosure pertains. In addition, terms defined in commonly used dictionary are not ideally or excessively interpreted unless explicitly defined otherwise.

As used herein, the term "pathogen" refers to microorganisms that cause diseases, such as viruses and bacteria. In general, pathogens include anything that may cause disease.

As used herein, the term bio-aerosol includes airborne microorganisms, microorganisms such as bacteria or mold, viruses, pollen causing allergy, etc., which are contained in gas or liquid particles.

Hereinafter, preferred embodiments of this disclosure will be described in detail with reference to the accompanying drawings.

FIG. 1A schematically illustrates a plasma generator according to an embodiment of this disclosure.

Referring to FIG. 1A, the plasma generator according to this disclosure includes a plasma generating module 1 that includes a first ground electrode 10, a high voltage electrode 30, and a first ceramic layer 20 made of a porous ceramic dielectric formed between the first ground electrode 10 and the high voltage electrode 30.

This disclosure is not limited thereto, but in the present application, dielectric barrier discharge may be most suitable to use large-area discharge in the form of electric discharge. The use of the dielectric barrier discharge has the advantage of obtaining a high concentration of active species per unit volume of the discharge area.

The first ground electrode 10 and the high voltage electrode 30 are made of a grid-like or porous metal such as a mesh. When power is applied to the high voltage electrode 30 by a high voltage power supply 40, a large amount of atmospheric pressure low-temperature plasma is generated at a portion in which the first ground electrode 10 and the high voltage electrode 30 are in contact with the dielectric ceramic. The metal is not limited thereto, but may include aluminum or stainless steel. With the above configuration, it is possible to effectively generate ozone for removing bacteria, viruses, etc., and it is possible to minimize pressure loss while increasing an air purification capacity.

A size and shape of the meshes of the first ground electrode 10 and the high voltage electrode 30 may be appropriately adjusted to prevent the dielectric ceramic bead from leaking out.

The overall shape of the first ground electrode 10 and the high voltage electrode 30 may be a rectangular frame, but a shape of the frame may be changed according to a configuration of a conventionally applied air conditioner.

The ceramic includes an antibacterial coating layer coated with an antibacterial material, and the ceramic layer is provided with open pores. With the above configuration, it is possible to effectively generate ozone for removing bacteria, viruses, etc., and it is possible to minimize pressure loss while increasing an air purification capacity.

The first ceramic layer is provided with the open pores, and thus, gas permeability is excellent.

The plasma generating module 1 may further include a second ceramic layer 22 made of a porous ceramic dielectric provided on one side of the high voltage electrode 30, and a second ground electrode 12 formed on one side of the second ceramic layer 22. The high voltage electrode 30, the second ceramic layer 22, and the second ground electrode 12 may increase a portion in contact with the porous ceramic dielectric to generate a large amount of atmospheric pressure low-temperature plasma.

With the above configuration, it is possible to effectively generate ozone for removing bacteria, viruses, etc., and it is possible to minimize pressure loss while increasing an air purification capacity.

A porosity (ratio of space volume to total volume) of the first ground electrode 10, the high voltage electrode 30, and the second ground electrode 12 may be 5 to 95 vol %. Although not limited thereto, when the porosity of the first ground electrode 10, the high voltage electrode 30, and the second ground electrode 12 is less than 5 vol %, the pressure loss increases, and when the porosity of the first ground electrode 10, the high voltage electrode 30, and the second ground electrode 12 exceeds 95 vol %, plasma generation for collection and sterilization of the bio-aerosol may not be smoothly performed.

The thickness of the first ground electrode 10, the high voltage electrode 30, or the second ground electrode 12 may be 0.1 to 10 mm. Although not limited thereto, when the thickness of the first ground electrode 10, the high voltage electrode 30, or the second ground electrode 12 is less than 0.1 mm, it is difficult to mechanically support the ceramic, and when the thickness of the first ground electrode 10, the high voltage electrode 30, or the second ground electrode 12 exceeds 10 mm, the first ground electrode 10, the high voltage electrode 30, or the second ground electrode 12 may take up more volume than necessary.

At least one of the first ceramic layer 20 and the second ceramic layer 22 may be formed as a single layer. With the above configuration, a large amount of atmospheric pressure low-temperature plasma may be generated by increasing a portion where the high voltage electrode 30 and the like is in contact with the porous ceramic dielectric. Accordingly, it is possible to efficiently remove pathogens, increase air purification capacity, and minimize pressure loss.

The ceramic layers 20 and 22 are for improving the removal efficiency of pathogens and contaminants by plasma, and the ceramics are not limited thereto, but may include at least one of alumina ($Al_2O_3$), zirconia ($ZrO_2$), diatomaceous earth, and silica ($SiO_2$).

An antibacterial coating layer of the ceramic may include at least one of zinc oxide having antibacterial activity and a carbon compound converting ozone into hydroxide. The zinc oxide and carbon compound may supply hydrogen peroxide or OH active species to the bio-aerosol collected in the ceramic layer to induce a sterilization effect and reduce ozone generated by plasma.

In addition, it may function as a ceramic filter coated with an antibacterial material that may implement antibacterial properties even under conditions in which plasma and ozone are not generated.

The zinc oxide may include ZnOx, wherein x may be 1 to 2.

When the zinc oxide is coated on the surface of the porous ceramic, it may have a sterilization effect by a photocatalytic function by light, and may destroy cell walls of bacteria by ion substitution. In addition, it is possible to increase sterilization power against bacteria collected on the surface of the plasma module. In addition, the zinc oxide may have an antibacterial effect of sterilizing infectious bacteria attached to the air purifier for a long time.

The carbon compound converts ozone into an OH active species to lower the concentration of ozone and increase the sterilization activity. The carbon compound may exhibit a complex function by impregnating an antibacterial and dustproof material into granular activated carbon (AC). The granular activated carbon may form a surface layer of the high voltage electrode with fine particles in a colloidal form. Examples of the carbon compound may include zeolite or activated carbon.

According to an embodiment, the ceramic may be a bead or a reticulated porous ceramic.

According to an embodiment, the plasma generator of the present application may include a first ceramic layer made of bead and a second ceramic layer made of bead; a first ceramic layer made of bead and a second ceramic layer made of reticulated porous ceramic; a first ceramic layer made of reticulated porous ceramic and a second ceramic layer made of bead; or a first ceramic layer made of reticulated porous ceramic and a second ceramic layer made of reticulated porous ceramic.

Figure 1B:
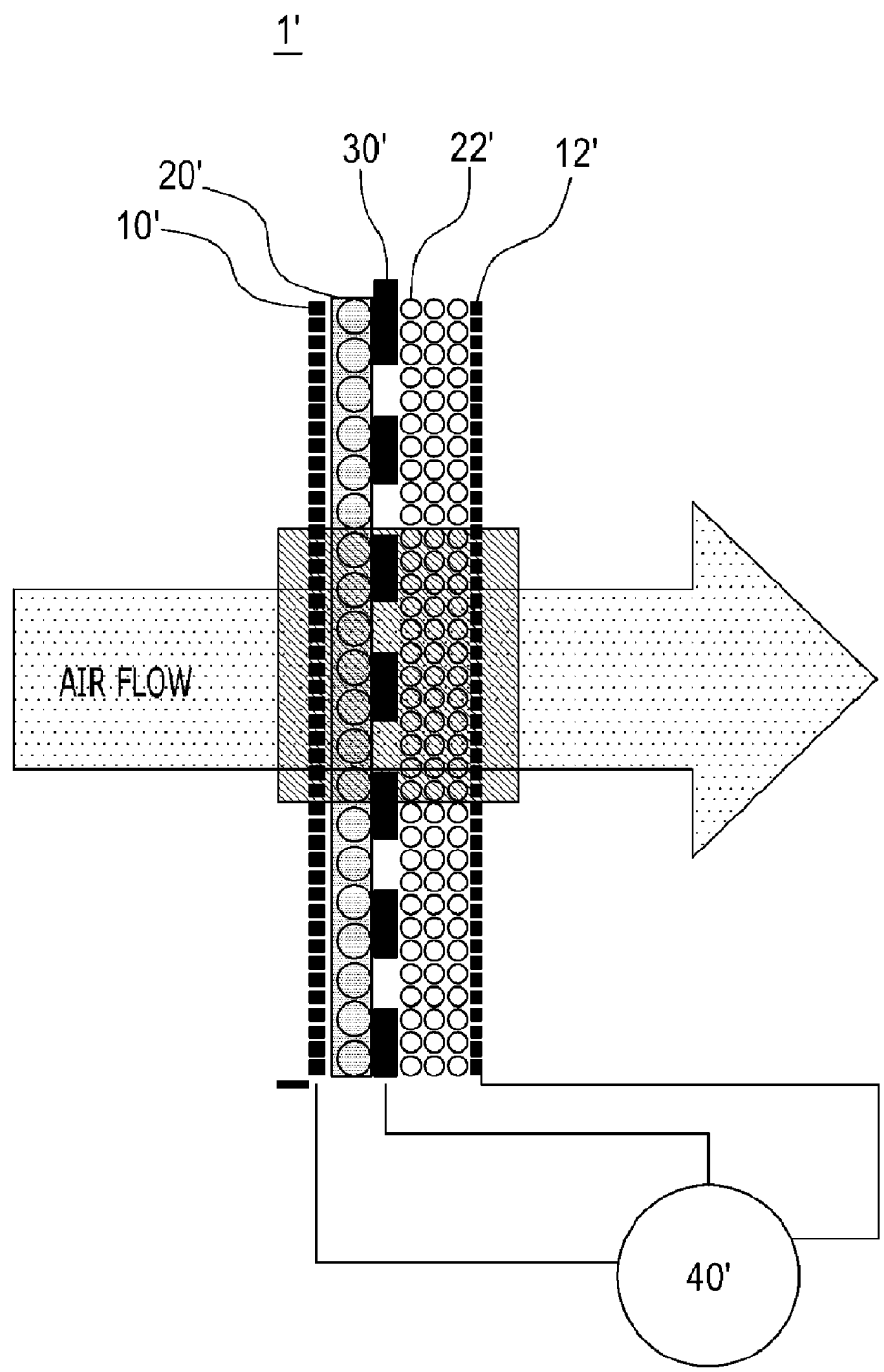
FIG. 1B is a diagram schematically illustrating a plasma generator according to another embodiment of this disclosure.

FIG. 1B illustrates a plasma generator including a first ceramic layer 20' made of bead and a second ceramic layer 22' made of reticulated porous ceramic.

The ceramic layers 20 and 22 according to the present application are formed as a single layer of porous ceramic, and a particle size of bead in the ceramic layers 20 and 22 may match a thickness of the ceramic layers 20 and 22. The particle size of the bead is correlated with the concentration of pathogens and the amount of ozone removed, and when the concentration is high, the particle size of the bead may be decreased to increase a surface area. The bead in the ceramic layers 20 and 22 typically has a larger diameter than an opening in the high voltage electrode 30 or the like. The ceramic layers 20 and 22 may be fixed by an adhesive or a mechanical fastening structure, and may be included before attachment to the high voltage electrode 30 etc., by assembly.

The particle size of the bead may be 100 to 5000 μm, and although not limited thereto, it may be suitable to increase pathogen removal efficiency and ozone removal efficiency.

A porosity of at least one of the first ceramic layer 20 made of the bead and the second ceramic layer 22 made of the bead may be 0.5 to 50 vol %. Although not limited thereto, when the porosity of the first ceramic layer 20 and the second ceramic layer 22 is less than 0.5 vol %, the pressure loss increases, and when the porosity of the first ceramic layer 20 and the second ceramic layer 22 exceeds 50 vol %, the collection and sterilization of the bio-aerosol are difficult or the air purification capacity may be reduced.

The pore distribution of the reticulated porous ceramic may be 30 to 100 pores per inch (PPI). Although not limited thereto, when the porosity distribution of the first ceramic layer 20 and the second ceramic layer 22 is less than 30 PPI, the pressure loss may increase, and when the porosity distribution of the first ceramic layer 20 and the second ceramic layer 22 exceeds 100 PPI, the collection and sterilization of the bio-aerosol may be difficult or the air purification capacity may be reduced.

The porosity of at least one of the first ceramic layer 20 made of the reticulated porous ceramic and the second ceramic layer 22 made of the bead may be 0.5 to 50 vol %.

The porosity of at least one of the first ceramic layer 20' made of the bead and the second ceramic layer 22' made of the reticulated porous ceramic may be 0.5 to 50 vol %.

Hereinafter, an air purifier according to an embodiment of this disclosure will be described in detail.

Since the air purifier of this disclosure can be manufactured in the form of a module, the air purifier of this disclosure may be easily applied to commercial air conditioning facilities in the form of being embedded in an air conditioning duct of a large facility such as a hospital.

That is, the air purifier of this disclosure includes a housing having an inlet, an outlet, and an air flow path connecting the inlet and the outlet; a plasma generator according to this disclosure; and a power supply unit for applying power to the plasma generator.

In addition, the air purifier of this disclosure is installed in a hospital and collects and sterilizes bio-aerosols according to characteristics of each space in a large space in air introduced into the interior and/or air emitted to the outside to effectively remove pathogens, thereby effectively preventing or managing in-hospital infections. In addition, the air purifier may efficiently remove ozone generated by plasma before discharging the ozone.

The air purifier of this disclosure may further include an ozone removal catalyst unit behind the plasma generator. The known catalyst capable of decomposing ozone may be used for the ozone removal catalyst unit. For example, it may be a filter including an ozone removal catalyst or an ozone decomposition catalyst in which a carbon composite, activated carbon particles, manganese dioxide, copper oxide and/or an active material are supported on a support containing Pd and/or Pt, but is not limited thereto.

The air flow rate in the air purifier may be adjusted for the purpose of this disclosure, that is, to increase pathogen removal efficiency and reduce ozone generated through a plasma generator. As a limitation, the wind speed of the air purifier may be 0.1 to 5 m/s.

The plasma generator included in the air purifier may be one frame or a frame assembled to form a predetermined area, but is not limited thereto, but the area of the plasma generation may be 100 to 3600 $cm^2$. When included in the area range, there is an advantage that can be easily applied to commercial air conditioning facilities already installed in large-scale buildings by controlling the area of the plasma generator within the range.

Figure 2A:
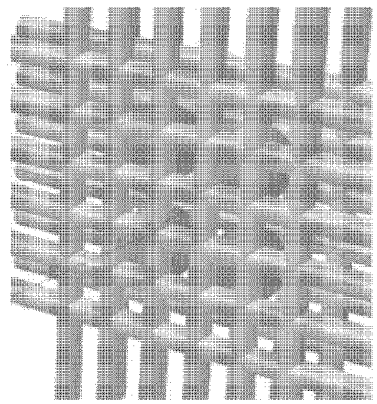
FIG. 2A is a schematic diagram of a plasma generating module according to an embodiment of this disclosure.
Figure 2A:
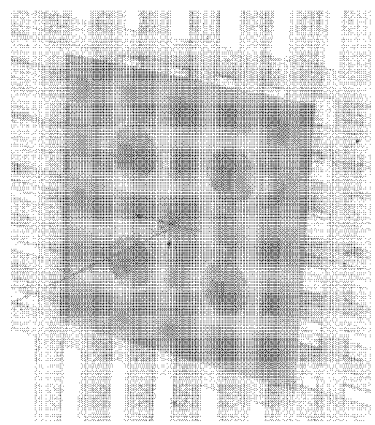
Figure 2B:
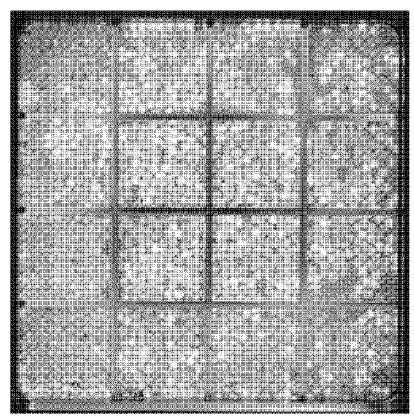
FIG. 2B is a photograph of a plasma generating module according to an embodiment of this disclosure.

Measurement of Ozone Generation Efficiency and Ozone Concentration of Plasma Generator The plasma generator (FIGS. 2A and 2B) of this disclosure was manufactured, and the ozone generation efficiency and ozone concentration were measured using the following calculation formulas and conditions.

Ozone generation efficiency [g/kWh]=Concentration of ozone [$g/m^3$]×flow rate [$m^3$/min]/power consumption [kW]×60 [min/h]

Ozone generation amount [ppm·$m^3$/min=$g/m^3$·$m^3$/min=g/min]=concentration of ozone [$g/m^3$]×flow rate [$m^3$/min]

Fixed variable: Flow rate=0.6[$m^3$/min]

Figure 3:
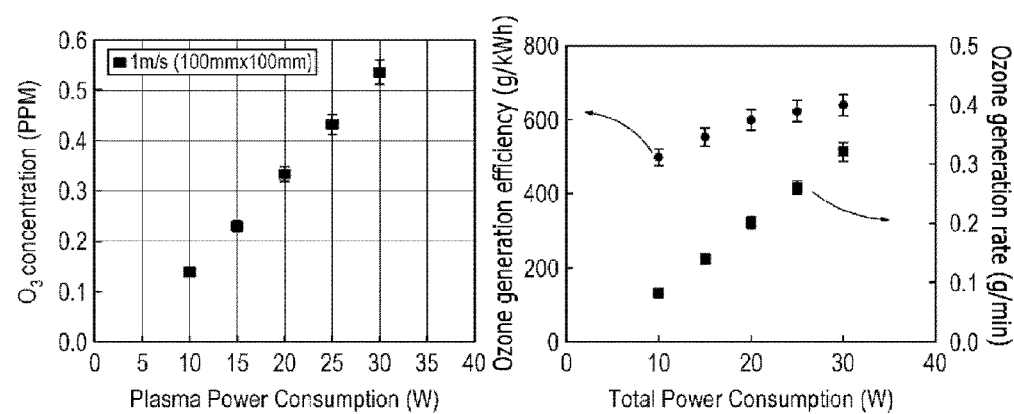
FIG. 3 is a graph illustrating results of measuring an ozone concentration and ozone generation efficiency by the plasma generator according to the embodiment of this disclosure.

Measurement value: Concentration of ozone (UV absorption-based ozone concentration meter), power consumption (power output from power supply), averaged after 3 or more evaluations for each condition The results are illustrated in FIG. 3. FIG. 3 is a graph illustrating results of measuring the ozone concentration and ozone generation efficiency by the plasma generator according to the embodiment of this disclosure.

In a general ozone generator, the ozone generation amount increases as the length of the plasma generator for ozone generation increases, but the decomposition degree of the generated ozone also increases. Therefore, the ozone generator that requires a concentration of ozone of several hundred ppm has a value of 100 g/kWh or less.

On the other hand, in the plasma generator according to this disclosure, the plasma generating unit is short with a few centimeters, and as illustrated in FIG. 3, it was confirmed that the ozone generation efficiency and the ozone concentration were remarkably improved. When the concentration of ozone for sterilization of bacteria in the air bio-aerosol is 0.5 ppm and the exposure time is less than 10 minutes, it shows 99.9% sterilization properties of *Escherichia coli, Staphylococcus aureus, Legionella*, etc. The concentration of ozone of the air conditioning gas desired in this disclosure is 0.5 ppm, and it is designed so that the bacteria in the bio-aerosol collected by the porous ceramic are exposed to ozone for several minutes or more. It is designed to be exposed for more than a few minutes at a low concentration of ozone of 0.5 ppm, and thus, the target concentration of ozone is low, so it shows excellent performance near the theoretical ozone generation efficiency limit value of 600~700 g/kWh (Reference: Vacuum 155 (2018) 29-37).

Evaluation of Ozone Generation and Emission Ozone Removal Characteristics of Air Purifier When the ozone removal catalyst unit is provided, it is possible to effectively reduce the concentration of ozone generated by the plasma generator. The following is an embodiment in which the ozone gas generated by the plasma generating module is treated with the ozone removal catalyst unit to lower the concentration of ozone emitted. Ozone gas of 0.97 ppm was generated by applying power to the plasma module in the environment in which air with a temperature of 21° C. and a humidity of 45% moved at a wind speed of 1 m/s in an air conditioning duct with a cross-sectional area of 100 cm$^2$. As a result of treating ozone gas at a temperature of 177° C. and a space velocity of 288,000/h by disposing a carbon composite-based ozone removal catalyst at the rear end of the plasma module, the concentration of ozone of 0.4 ppm was confirmed. Considering that the reduced concentration compared to the initial input ozone gas is 0.57 ppm, the ozone gas having a concentration of about 0.5 ppm using the ozone removal catalyst applied in this embodiment will be able to maintain the concentration of ozone emitted below 0.05 ppm.

Evaluation of Antibacterial Properties of Plasma Generator

After coating on the flexible dielectric using the ZnO-based antibacterial material of this disclosure, the antibacterial properties were evaluated. The results were shown in Tables 1 to 3.

Table 1 showed the results of confirming the antibacterial ability of the ZnO-based antibacterial material, and was evaluated using the JIS Z 2801 standard. It was confirmed that *Staphylococcus aureus* and *Escherichia coli* were reduced by more than 99.9% by the ZnO-based antibacterial material.

Table 2 showed the results of evaluating the antibacterial ability of the ZnO-based antibacterial material according to ASTM E 2180 standard which is a favorable condition for bacterial propagation compared to the conditions in Table 1. It was confirmed that *Staphylococcus aureus* and *Klebsiella pneumonia* were reduced by more than 99.9% after 24 hours by the ZnO-based antibacterial material.

Table 3 showed the results of evaluating the antibacterial ability of ZnO-based antibacterial materials according to ASTM E 2149 standard to confirm the antibacterial properties in a shorter time than the conditions in Table 2. It was confirmed that *Escherichia coli* was reduced by more than 99.9% after 1 hour by the ZnO-based antibacterial material.

Therefore, when the ZnO-based antibacterial material is coated inside the air purifier, it is possible to obtain the excellent antibacterial effect, and maximize the sterilization effect together with the ozone generated by the plasma generating module.

Although the specific embodiments according to this disclosure have been described so far, various modifications are possible without departing from the scope of this disclosure. Therefore, the scope of this disclosure is not limited to the described embodiments, and should be defined by the claims described below and their equivalents.

TABLE 1

| | | | 2 h | 4 h | | 24 h | |
| Incubation time (Contact time) | | Reference | | | | | |
| Specimen | | (Untreated sample) | ZnO | Reference | ZnO | Reference | ZnO |
|---|---|---|---|---|---|---|---|
| *Staphylococcus aureus* (S. aureus) | Initial number of bacteria (Number of bacteria/cm$^2$) | $2.2 \times 10^4$ | $1.4 \times 10^4$ | $2.2 \times 10^4$ | $1.4 \times 10^4$ | $1.4 \times 10^4$ | $1.4 \times 10^4$ |
| | After incubation (Number of bacteria/cm$^2$) | $4.4 \times 10^2$ | <0.63 | $1.2 \times 10^3$ | <0.63 | $2.6 \times 10^4$ | <0.63 |
| | Bacterial reduction rate (%) | — | 99.9 | — | 99.9 | — | 99.9 |
| *Escherichia coli* (E. coli) | Initial number of bacteria (Number of bacteria/cm$^2$) | $2.5 \times 10^4$ | $1.7 \times 10^4$ | $2.5 \times 10^4$ | $1.7 \times 10^4$ | $1.7 \times 10^4$ | $1.7 \times 10^4$ |
| | After incubation (Number of bacteria/cm$^2$) | $1.5 \times 10^3$ | 3 | $1.3 \times 10^4$ | <0.63 | $1.1 \times 10^6$ | <0.63 |
| | Bacterial reduction rate (%) | — | 99.8 | — | 99.9 | — | 99.9 |

TABLE 2

| | | Reference | ZnO |
|---|---|---|---|
| *Staphylococcus aureus* (S. aureus) | Initial number of bacteria (Number of bacteria/cm$^3$) | $2.3 \times 10^6$ | $1.4 \times 10^4$ |
| | After 24 hours (Number of bacteria/cm$^2$) | $2.8 \times 10^6$ | <0.63 |
| | Bacterial reduction rate (%) | — | 99.9 |
| *Klebsiella pneumonia* (K. Pneumonia) | Initial number of bacteria (Number of bacteria/cm$^2$) | $2.7 \times 10^6$ | $1.7 \times 10^4$ |
| | After 24 hours (Number of bacteria/cm$^3$) | $3.5 \times 10^7$ | <0.63 |
| | Bacterial reduction rate (%) | — | 99.9 |

TABLE 3

| | | Reference | ZnO |
|---|---|---|---|
| *Escherichia coli* (E. coli) | Initial number of bacteria (Number of bacteria/cm$^2$) | $2.1 \times 10^5$ | $2.1 \times 10^5$ |
| | After one hour (Number of bacteria/cm$^3$) | $2.1 \times 10^5$ | <30 |
| | Bacterial reduction rate (%) | | 99.9 |

DESCRIPTION OF REFERENCE NUMERALS 1, 1': Plasma generating module
10, 10', 12, 12': Ground electrode
20, 20', 22, 22': Ceramic layer
30, 30': High voltage electrode
40, 40': High voltage power supply

The invention claimed is:

1. A plasma generator, comprising:
a plasma generating module comprising a first ground electrode, a high voltage electrode, and a first ceramic layer consisting of a porous ceramic dielectric formed between the first ground electrode and the high voltage electrode,
wherein the first ground electrode and the high voltage electrode are made of a grid-like or porous metal,
the porous ceramic dielectric consists of a plurality of beads comprising an antibacterial coating layer coated with an antibacterial material, and the first ceramic layer is provided with an open pore, and a particle size of the bead matches a thickness of the first ceramic layer.

2. The plasma generator of claim 1, wherein the plasma generating module further comprises a second ceramic layer made of a porous ceramic dielectric provided on one side of the high voltage electrode, and a second ground electrode provided on one side of the second ceramic layer.

3. The plasma generator of claim 1, wherein the plasma generating module further comprises a second ground electrode provided on one side of the high voltage electrode.

4. The plasma generator of claim 1, wherein a porosity of the first ground electrode and the high voltage electrode is 5 to 95 vol %.

5. The plasma generator of claim 1, wherein a thickness of the first ground electrode or the high voltage electrode is 0.1 to 10 mm.

6. The plasma generator of claim 1, wherein the first ceramic layer is formed as a single layer.

7. The plasma generator of claim 1, wherein the ceramic comprises at least one of alumina ($Al_2O_3$), zirconia ($ZrO_2$), diatomaceous earth, and silica ($SiO_2$).

8. The plasma generator of claim 1, wherein an antibacterial coating layer of the ceramic comprises at least one of zinc oxide having antibacterial activity and a carbon compound converting ozone into hydroxide.

9. The plasma generator of claim 8, wherein the zinc oxide comprises $ZnO_x$, wherein x is 1 to 2.

10. The plasma generator of claim 8, wherein the carbon compound converts ozone into OH active species.

11. The plasma generator of claim 2, wherein the porous ceramic dielectric in the second ceramic layer has a pore density of 30 to 100 pores per inch (PPI).

12. The plasma generator of claim 1, wherein a particle size of the bead is 100 to 5000 μm.

13. The plasma generator of claim 2, wherein a porosity of at least one of the first ceramic layer and the second ceramic layer is 0.5 to 50 vol %.

14. An air purifier comprising the plasma generator of claim 1.

15. The air purifier of claim 14, further comprising:

an ozone removal catalyst unit behind the plasma generator.

16. The air purifier of claim 14, wherein a wind speed of the air purifier is 0.1 to 5 m/s.

* * * * *